United States Patent [19]

Motai et al.

[11] Patent Number: 4,879,235

[45] Date of Patent: Nov. 7, 1989

[54] PROCESS FOR PRODUCING PROTEASE BY CULTIVATING A PROTEASE-PRODUCING MOLD IN A LIQUID MEDIUM

[75] Inventors: Hiroshi Motai; Yaichi Fukushima, both of Noda; Tetsuro Fukase; Harumichi Itoh, both of Atsugi, all of Japan

[73] Assignee: The Japanese Research and Development Association for Bioreactor System, Tokyo, Japan

[21] Appl. No.: 933,177

[22] Filed: Nov. 21, 1986

[30] Foreign Application Priority Data

Nov. 29, 1985 [JP] Japan ................................ 60-267326
Dec. 27, 1985 [JP] Japan ................................ 60-292988

[51] Int. Cl.[4] .......................... C12N 9/62; C12N 9/50; C12N 9/60; C12N 1/16

[52] U.S. Cl. .................................... 435/225; 435/219; 435/224; 435/254; 435/255; 435/913; 435/918

[58] Field of Search ............... 435/219, 213, 224, 225, 435/254, 913, 918, 255

[56] References Cited

U.S. PATENT DOCUMENTS 4,480,036 10/1984 Morgan et al. ..................... 435/220

FOREIGN PATENT DOCUMENTS 2211175 7/1975 Japan .
9518076 8/1976 Japan .
1279777 4/1977 Japan .

OTHER PUBLICATIONS

Cohen, B. L. et al., (1975), Arch. Biochem. Biophys 169, 324–330.

Hanson, M. A. et al., (1973) J. Bacteriol. 116(2) 785–789.

Hislop, E. C. et al. (1982), J. Gen. Microbiol. 128, 799–807.

Koltun, L. V. et al., (1986), Chem. Abstracts, 104:221708e.

M. D. Lilly in *Applied Biochem and Bioeng.,* vol. 2, Enzyme Technology (Wingarb et al. ed), Acad. Press., N.Y., (1979), pp. 6–9, 18–21.

*Primary Examiner*—Thomas G. Wiseman
*Assistant Examiner*—Charles L. Patterson, Jr.
*Attorney, Agent, or Firm*—Banner, Birch, McKie & Beckett

[57] ABSTRACT

A process for producing protease by cultivating a protease-producing mold in a liquid medium, which is characterized by continuously adding a liquid medium containing a protein material to the culture medium after the substantial termination of proliferation of the mold cells.

5 Claims, 1 Drawing Sheet

× PROTEASE ACTIVITY
○ CELL CONCENTRATION
CULTIVATION TIME
(DAYS)
0
2
4
6
8
10
12
14
16
CELL CONCENTRATION (g/ℓ)
0
5
10
15
20
PROTEASE ACTIVITY (PU/mℓ)
0
100
200
300
400
500

PROCESS FOR PRODUCING PROTEASE BY CULTIVATING A PROTEASE-PRODUCING MOLD IN A LIQUID MEDIUM

BACKGROUND OF THE INVENTION

1. Field of the Invention:

This invention relates to a process for the efficient production of high-potency protease by use of protease-producing molds.

2. Description of the Prior Art:

Protease is a hydrolase capable of acting upon proteins or the hydrolyzates thereof to split the peptide link. Protease is widely used in pharmaceuticals, fermentation foods, detergents, and the like.

Prior studies on the production of protease by the use of microorganisms have aimed principally at the screening or breeding of microorganisms having a high protease-producing activity. The studies concerning the cultivating conditions have also been confined to the composition of media such as the addition of inorganic salts to the media (e.g. Japanese Patent Publication No. 22,111/75) and the type of nitrogen source [e.g. Japanese Patent Application "Kokai" (Laid-open) No. 95,180/76] or carbon source (e.g. Japanese Patent Publication No. 12,797/77). Furthermore, the proposed processes have invariably been batch processes.

Chiefly because of a batch process, every proposed process produces protease only in the stationary phase succeeding the proliferation of mold cells. Moreover, there are problems such that owing to the difficulty in controlling the carbon and nitrogen sources in the medium during the stationary phase, the time period for the efficient production of protease is short and also the potency of collected protease is comparatively low.

SUMMARY OF THE INVENTION

The present invention is directed to solve the problems of prior processes and the primary object is to provide a process for the efficient production of high-potency protease.

According to this invention, there is provided a process for producing protease by the cultivation of a protease-producing mold in a liquid medium, which is characterized by continuing the cultivation after the terminal phase of proliferation of mold cells, while continuously adding a liquid medium containing a protein material.

BRIEF DESCRIPTION OF THE DRAWING

The accompanying drawing shows diagrams representing the progress of cultivation.

DETAILED DESCRIPTION OF THE INVENTION

Figure 1:
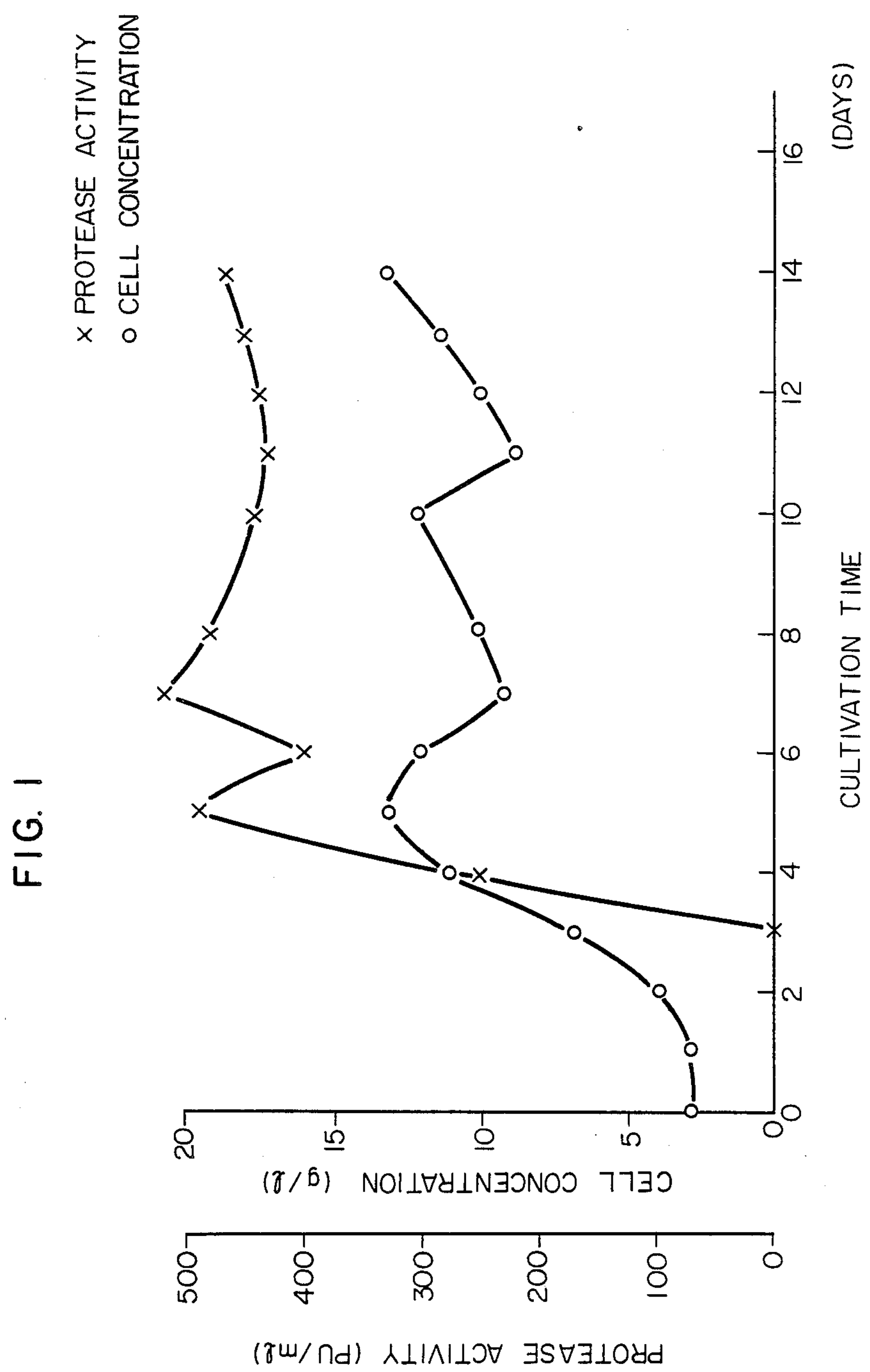

The molds capable of producing protease according to this invention are those protease-producing molds belonging, for example, to genera Aspergillus, Penicillium, Mucor, and Rhizopus. As examples mention may be made of *Aspergillus sojae* ATCC 20823 (IAM 2703), *Aspergillus sojae* IAM 2631, *Aspergillus oryzae* ATCC 20822 (IAM 2609), *Aspergillus oryzae* IFO 4176, *Aspergillus tamarii* IAM 2156, *Penicillium chrysogenum* HUT 4019, *Penicillium luteum* AHU 8022, *Mucor racemosus* AHU 6002, *Mucor himaelis* HUT 1131, *Rhizopus formosensis* IFO 4732, and *Rhizopus javanicus*, IFO 5441.

In the process of this invention, it is advantageous to use protease-producing halotolerant molds in view of keeping the culture from contamination with infections microbes (an approximate standard for the suitable halotolerance is 5, preferably 10, % or above in terms of sodium chloride).

In the following description, the cultivation of molds before addition of the liquid medium containing protein materials, that is, the cultivation to proliferate the mold cells is referred to as precultivation.

The medium used in the precultivation can be any of the conventional liquid media used in the liquid culture of protease-producing molds. As examples of the carbon source in the media, there may be mentioned glucose, soluble starch, sucrose, dextrin, cellulose, glycerol, and wheat bran. Examples of nitrogen source are peptone, meat extract, yeast extract, soybean flour, rice bran, casein, polypeptone, and gluten. Examples of inorganic salts are various phosphoric acid salts, sulfates, and hydrochlorides. If necessary, vitamins and nucleic acids may be added to the medium.

After inoculation of protease-producing mold cells into the above liquid medium, the liquid cultivation is carried out. Although the cultivation conditions including cultivation temperature, pH of the medium, and the rate of aeration vary depending upon the type of mold strain being used and the composition of medium, there are generally used a cultivation temperature of 25° to 40° C., pH of the medium of 3 to 8, and the aeration rate of 0.1 to 2 V.V.M.

After the lag phase in the initial stage, the culture enters the proliferation phase and the proliferation of mold cells proceed very actively. After about 1 to 4 days from the beginning of cultivation, the proliferation usually comes nearly to termination and passes into substantially stationary phase.

According to the present invention, after termination of proliferation, that is, in the enzyme production period which substantially begins from the terminal stage of proliferation, a liquid medium containing a protein material is added continuously to the medium so that (1) the sugar concentration in the medium may become 0.10, preferably 0.05, % (W/V) or less and the nitrogen concentration may become 0.06 to 0.30% (W/V) or (2) the nitrogen concentration may become 0.05% (W/V) or less, independent of the sugar concentration.

As examples of protein materials used in the supplementary medium containing protein materials, there may be mentioned soybean, defatted soybean, separated soybean protein, milk casein, egg albumin, bovine serum albumin, wheat gluten, peptone, and soytone. These materials are used each alone or in mixtures of two or more. If necessary, to the liquid medium containing such a protein material, there can be added saccharide materials such as glucose, sucrose, lactose, galactose, soluble starch, dextrin, cellulose, and wheat; inorganic salts such as various phosphoric acid salts, sulfates, and hydrochlorides; vitamins and nucleic acids.

The reason for the addition of a supplementary liquid medium containing protein materials to the culture medium after substantial termination of the proliferation phase is as described below.

In the culture medium, with the proliferation of mold cells there are formed tiny amounts of protease, peptidase, and the like which decompose the proteins contained in the medium in the early period of cultivation into amino acids, thereby destroying the inducer of protease production. Owing to the substantial or complete nonexistence of proteins, the culture medium becomes unable to induce protease production and so the production of high-potency protease cannot be expected after the termination of proliferation of mold cells.

For this reason, in order to increase the production of protease, a liquid medium containing protein materials should be added to the culture medium after substantial termination of the proliferation. The present inventors conducted a detailed study on this problem and found that satisfactory results can be obtained by continuously adding a liquid medium containing a protein material to the culture medium after the substantial termination of the proliferation of mold cells so that (1) the saccharide concentration in the culture medium may become 0.10% (W/V) or less and the nitrogen concentration may become 0.06 to 0.30% (W/V) or (2) the nitrogen concentration may become 0.05% (W/V) or less.

In order to regulate the addition of a liquid medium containing a protein material to the culture liquor after the substantial termination of proliferation of mold cells so that the culture liquor will show the aforementioned saccharide concentration and nitrogen concentration, there are several means including adjustment of the medium composition, the rate of addition, and the ratio of liquid medium being added to the culture liquor, from which a suitable means can be selected. An example of preferred means is described below.

A saccharide source is decomposed by the mold to a monosaccharide which is a repression factor for the protease production. To alleviate such a difficulty, it is necessary to reduce the saccharide content of the medium relative to the protein content and the phosphorus content. Therefore, before formulating the composition of a liquid medium containing a protein material to be added to the culture liquor after substantial termination of proliferation, it is advantageous to conduct preliminary experimental culture of the protease-producing mold strain being used in order to find the proportions of saccharide, protein and other nutritive sources required to bring the residual nitrogen concentration to 0.06–0.3 % (W/V) when the saccharide source has been completely consumed.

A liquid medium containing a protein material and having a composition as determined by the above preliminary experiment is added to the culture liquor after substantial termination of proliferation so that the saccharide concentration of the culture liquor may become 0.10% (W/V) or below, preferably 0.05% (W/V) or below, thereby bringing the nitrogen concentration in the culture liquor within the range of from 0.06 to 0.30% (W/V).

When the liquid medium contains no saccharide, the liquid medium containing a protein material is added so that the nitrogen concentration in the culture liquor may become within the range of from 0.06 to 0.30% (W/V).

One of the means to keep the nitrogen concentration in culture liquor at 0.05% (W/V) or less is to reduce the proportion of nitrogen content in the carbon, nitrogen, and phosphorus contents of the protein-containing liquid medium, as compared with that in those of the mold cells themselves.

The nitrogen source in the medium is decomposed by the mold into amino acids which act as repressive factor for the protease production. It is necessary, therefore, to keep the nitrogen source content of the medium lower than the saccharide and phosphorus contents by taking into account the carbon, nitrogen, and phosphorus contents of the mold cells themselves. Before formulating the composition of a liquid medium containing a protein material to be added to the culture liquor after substantial termination of proliferation, it is advantageous to conduct preliminary experimental culture of protease-producing strain being used, in order to find the proportions of saccharide and other nutritive sources and protein so that the nitrogen source may be consumed earlier than carbon, phosphorus, and other nutritive sources.

A liquid medium containing a protein material and having a composition as determined above is added to the culture liquor after substantial termination of proliferation so that the nitrogen concentration of the culture liquor may become 0.05% (W/V) or less, thereby to keep the nitrogen concentration in the culture liquor at 0.05% (W/V) or less.

The addition of the liquid medium containing protein materials to the culture liquor after substantial termination of proliferation can be done either continuously or intermittently. Thus, the cultivation by adding a liquid medium containing protein materials to the culture liquor after substantial termination of proliferation is carried out by continuously adding said liquid medium and continuously withdrawing the culture liquor; or by intermittently adding said liquid medium and intermittently withdrawing the culture liquor; or by the method of feeding culture, wherein the liquid medium is added continuously or intermittently. In other respects, the continuous culture and feeding culture are carried out in a customary manner. In the cultivation method of intermittently adding the medium containing protein materials and intermittently withdrawing the culture liquor, the amount of addition and the amount of withdrawal can be the same or different; and the addition and withdrawal can be done simultaneously or not simultaneously.

In the above-mentioned cultivation methods, when the cultivation is carried out by continuously adding a liquid medium containing protein materials, generally the temperature is 25° to 35° C., pH of the medium is 3 to 8, and the rate of aeration is 0.1 to 2 V.V.M.

As described above, after the substantial termination of proliferation, the culture liquor is maintained, according to this invention, at a nitrogen concentration of 0.06 to 0.30% (W/V) and a saccharide concentration of 0.10% (W/V) or below, or a nitrogen concentration at 0.05% (W/V) or below. Such conditions are effective to minimize the formation of those monosaccharides or amino acids which inhibit the production of protease, thereby to promote markedly the production of protease. In addition, in the process of this invention, since proteins, which induce the protease formation, are continuously fed to the culture liquor according to this invention, the mold cells are always susceptible to the induction of protease formation, thereby allowing the mold cells to produce high-potency protease which is never obtained by the batch culture.

After completion of the cultivation, protease is collected from the culture liquor by filtration from the mold cells and, if necessary, purifying by dialysis, salting-out, ion exchange, or gel filtration.

Because of efficient production of high-potency protease, the process of this invention has high significance to the industrial field.

The advantage of the present invention is illustrated below with reference to Experimental Examples.

EXPERIMENTAL EXAMPLE 1

Comparison between batch culture and continuous culture.

A liquid medium (pH 6.5) containing 0.5% (W/V) of starch, 1.0% (W/V) of separated soybean protein, 0.5% (W/V) of $KH_2PO_4$, 0.05% (W/V) of $MgSO_4$, 100 ppm of $CaCl_2$, and 0.03% (W/V) of yeast extract was sterilized by heating in an autoclave at atmospheric pressure. The sterilized medium was poured into a jar fermenter and inoculated with a spore suspension ($10^6$/ml in number of spores) of *Aspergillus oryzae* ATCC 20822 (IAM 2609). The inoculated medium was cultivated (dissolved oxygen concentration (DO): 2 ppm; stirrer: 400 rpm) while adjusting pH to 6.3 with 5N sulfuric acid and 5N sodium hydroxide. After 48 hours (substantial termination of proliferation) from the beginning of liquid culture, continuous cultivation and batch cultivation were carried out as described below.

Continuous culture:

To the culture liquor, after 48 hours from the beginning of liquid culture, was fed continuously through the feed inlet of the jar fermenter a liquid medium [prepared by heat-sterilizing in an autoclave at atmospheric pressure a liquid medium, pH 6.5, containing 0.5% (W/V) of starch, 1.0% (W/V) of separated soybean protein, 0.5% (W/V) of $K_2HPO_4$, 0.05% (W/V) of $MgSO_4$, 100 ppm of $CaCl_2$, and 0.03% (W/V) of yeast extract] at a rate of 0.02 V/V.hr (dilution ratio), while continuously withdrawing an equal volume of culture liquor from the jar fermenter through the outlet. The continuous culture was continued until the seventh day from the beginning of the initial liquid culture and the collected culture liquor was used for testing. During the continuous culture, DO was maintained at 2 ppm and the stirrer speed at 400-600 rpm. On and after the third day from the initial liquid culture, the culture liquor was maintained at a saccharide concentration of 0.005-0.025% (W/V) and a nitrogen concentration of 0.08-0.12% (W/V).

Batch culture:

The culture liquor on and after 48 hours from the beginning of the aforementioned liquid culture was subjected to batch culture, without the addition of a liquid medium containing protein materials, under the conditions: temperature, 30° C.; pH of the medium 6.5; DO, 2 ppm; speed of stirrer 400-600 rpm. The batch culture was continued until the seventh day from the beginning of initial liquid culture, while withdrawing the sample of culture liquor once a day for use as control. During the cultivation on and after the third day from the beginning of initial liquid culture, the culture liquor showed a saccharide concentration of 0.001-0.030% (W/V) and a nitrogen concentration of 0.07-0.11% (W/V).

The test samples and control samples obtained above were assayed for the protease potency (P.U./ml) by the modified method of Anson - Ogiwara [Agr. Biol. Chem., Vol. 37, p. 2703 (1973)]; and the same applies hereinafter. The results of assay were as shown in Table 1.

TABLE 1

| | Number of days | | | | | | |
|---|---|---|---|---|---|---|---|
| Sample | 1 | 2 | 3 | 4 | 5 | 6 | 7 |
| Test sample | 10 | 50 | 180 | 280 | 350 | 500 | 500 |
| Control sample | 10 | 30 | 150 | 200 | 190 | 190 | 185 |

From the results shown in Table 1, it is seen that as compared with the batch process, the continuous process of this invention efficiently produced protease of a far higher potency for an extended period of time.

EXPERIMENTAL EXAMPLE 2

Comparison between the method (method of this invention) of continuous culture by the addition of a liquid medium containing protein materials and the method (control method) of continuous culture by the addition of a liquid medium containing no protein materials:

The method (method of this invention) of continuous culture by the addition of a liquid medium containing protein materials was carried out in the same manner as in Experimental Example 1. The culture liquor collected by continuous withdrawing was used as test sample.

The method (control method) of continuous culture by the addition of a liquid medium containing no protein materials was carried out in the same manner as in Experimental Example 1, except that the additional liquid medium contained 1.0% (W/V) of Casamino acid in place of 1.0% (W/V) of the separated soybean protein used in Experimental Example 1. The culture liquid collected by continuous withdrawing was used as control sample. After 3 days from the beginning of initial liquid culture, the culture liquor showed a saccharide concentration of 0.005 to 0.030% (W/V) and a nitrogen concentration of 0.08 to 0.15% (W/V).

The test sample and the control sample were assayed for the potency of protease. The results obtained were as shown in Table 2.

TABLE 2

| | Number of days | | | | | | |
|---|---|---|---|---|---|---|---|
| Sample | 1 | 2 | 3 | 4 | 5 | 6 | 7 |
| Test sample | 10 | 50 | 180 | 280 | 350 | 500 | 500 |
| Control sample | 10 | 30 | 100 | 120 | 120 | 105 | 110 |

From the results shown in Table 2, it is seen that as compared with the method (control) of continuous culture by the addition of a liquid medium containing no protein materials, the method (method of this invention) of continuous culture by the addition of a liquid medium containing protein materials efficiently produced protease of a far higher potency for an extended period of time.

EXPERIMENTAL EXAMPLE 3

Test on carbon concentration in culture liquor after substantial termination of proliferation.

Continuous culture was carried out in the same manner as in Experimental Example 1, except that the dilution ratio was 0.04 V/V.hr. The continuously withdrawn culture liquor was used as test sample (the method of this invention). The culture liquor after 3 days from the beginning of initial liquid culture showed a saccharide concentration of 0.005 to 0.040% (W/V) and a nitrogen concentration of 0.08 to 0.15% (W/V).

Another continuous culture was run in the same manner as described above, except that 5.0% (W/V) of starch was added in place of 0.5% (W/V) of starch. The continuously withdrawn culture liquor was used as control (control method). After 3 days from the beginning of initial liquid culture, the culture liquor showed a saccharide concentration of 0.15 to 0.30% (W/V) and a nitrogen concentration of 0.06 to 0.08% (W/V).

The results of assay for the potency of protease performed on the test sample and the control sample were as shown in Table 3.

TABLE 3

| Sample | Number of days 1 | 2 | 3 | 4 | 5 | 6 | 7 |
|---|---|---|---|---|---|---|---|
| Test sample | 10 | 40 | 160 | 200 | 250 | 450 | 450 |
| Control sample | 5 | 10 | 25 | 50 | 55 | 55 | 60 |

From the results shown in Table 3, it is seen that as compared with the control method, the method of this invention efficiently produced protease of a far higher potency for an extended period of time.

The invention is illustrated below with reference to Examples, but the invention is not limited thereto.

EXAMPLE 1

A liquid medium, pH 7.0, containing 1.0% (W/V) of polypeptone, 0.5% (W/V) of starch, 0.5% (W/V) of $KH_2PO_4$, 0.05% (W/V) of $MgSO_4$, 0.03% (W/V) of yeast extract, and 10% (W/V) of sodium chloride was sterilized by heating at 120° C. for 10 minutes. Into a 3-liter jar fermenter, was charged 2 liters of the sterilized liquid medium. The liquid medium was then inoculated with a spore suspension (number of spores: $1.0\times10^6$/ml) of *Aspergillus sojae* ATCC 20823 (IAM 2703) collected from a slant culture in malt extract medium. The inoculated medium was cultivated at 30° C. and an aeration rate of 1 V.V.M. with stirring at 500 rpm. The pH of the culture medium during cultivation was adjusted to 7.0 with 5N $H_2SO_4$ and 5N NaOH.

When 48 hours had elapsed after the beginning of cultivation (that is, when proliferation of mold cells had been substantially terminated), continuous addition of a protein-containing liquid medium of the following composition was commenced at a dilution ratio of 0.02 (V/V.hr):

| | % (W/V) |
|---|---|
| Separated soybean protein | 1.0 |
| $KH_2PO_4$ | 0.5 |
| Soluble starch | 0.5 |
| $MgSO_4$ | 0.05 |
| Yeast extract | 0.03 |
| Sodium chloride | 10. |
| pH of the medium: 7.0 | |
| Sterilization at 120° C. for 10 min. | |

The cultivation was continued under the following conditions:

| | |
|---|---|
| Temperature | 30° C. |
| pH of the culture medium | 7.0 |
| Rate of aeration | 1 V.V.M |
| Stirring | 400–600 rpm |

On and after the third day of cultivation, the culture liquor showed a saccharide concentration of 0.005 to 0.030% (W/V) and a nitrogen concentration of 0.09 to 0.12% (W/V). A protease-containing culture liquor of the same volume as that of continuously added medium was continuously obtained from the outlet of jar fermenter. The culture liquor thus obtained was assayed for the protease potency. The results obtained were as shown in Table 4.

TABLE 4

| Number of days | 1 | 2 | 3 | 4 | 5 | 6 |
|---|---|---|---|---|---|---|
| Potency (P.U./ml) of protease in culture liquor | 20 | 50 | 280 | 320 | 490 | 500 |

EXAMPLE 2

A liquid medium, pH 6.5, containing 0.75% (W/V) of soluble starch, 1.33% (W/V) of polypeptone, 0.5% (W/V) of $KH_2PO_4$, 0.5% (W/V) of $MgSO_4$, and 0.03% (W/V) of yeast extract was sterilized at 120° C. for 10 minutes. Into a 3-liter fermenter, was charged 1.0 liter of the sterilized liquid medium. The liquid medium was then inoculated with a spore suspension (number of spores: $1.2\times10^6$/ml) of *Aspergillus oryzae* ATCC 20822 (IAM 2609) collected from a slant culture in malt extract medium. The inoculated medium was cultivated at 30° C. and an aeration rate of 1 V.V.M. with stirring at 500 rpm. The pH of the culture medium during cultivation was adjusted to about 6.5 with 5N $H_2SO_4$.

When 72 hours had elapsed after the beginning of cultivation (that is, when proliferation of mold cells has been substantially terminated), continuous addition of a protein-containing liquid medium of the following composition was commenced at a feeding rate of 10 ml/hour through a silicone tube.

| | % (W/V) |
|---|---|
| Defatted soybean flour | 1.5 |
| Soluble starch | 0.75 |
| $KH_2PO_4$ | 0.5 |
| $MgSO_4$ | 0.5 |
| Yeast extract | 0.03 |
| Sterilization at 120° C. for 10 minutes | |

The cultivation was continued under the following conditions:

| | |
|---|---|
| Temperature | 30° C. |
| pH of the culture medium | 7.0 |
| Rate of aeration | 1 V.V.M. |
| Stirring | 400–600 rpm |

A protease-containing culture liquor was obtained during 3 days of cultivation [the saccharide concentration in the culture medium was 0.005 to 0.040% (W/V) and the nitrogen concentration was 0.07 to 0.12% (W/V)]. The protease potency of the culture liquor thus obtained was 600 P.U./ml.

EXAMPLE 3

A liquid medium (pH 6.5) containing 0.75% (W/V) of soluble starch, 1.33% (W/V) of polypeptone, 0.5% (W/V) of $KH_2PO_4$, 0.5% (W/V) of $MgSO_4$, and 0.03% (W/V) of yeast extract was sterilized at 120° C. for 10 minutes. Into a 3-liter fermenter, was charged 1.0 liter of the sterilized liquid medium. The liquid medium was then inoculated with a spore suspension (number of spores: $1.2\times10^6$/ml) of *Aspergillus oryzae* ATCC 20822 (IAM 2609) collected from the malt extract medium of a slant culture. The inoculated medium was cultivated at 30° C. and an aeration rate of 1 V.V.M. with stirring at 500 rpm. The pH of the culture medium during cultivation was continually adjusted to about 6.5 with 5N $H_2SO_4$.

When 72 hours had elapsed after the beginning of cultivation (that is, when proliferation of mold cells had been substantially terminated), 120 ml of a protein-containing liquid medium (pH 6.5) of the following composition was added to the culture liquor:

| | % (W/V) |
|---|---|
| Defatted soybean flour | 1.5 |
| Soluble starch | 0.75 |
| $KH_2PO_4$ | 0.5 |
| $MgSO_4$ | 0.5 |
| Yeast extract | 0.03 |
| Sterilization at 120° C. for 10 minutes. | |

The cultivation was continued for 3 days under the following conditions, while adding 120 ml of said protein-containing liquid medium every 12 hours:

| | |
|---|---|
| Temperature | 30° C. |
| pH of the culture medium | 7.0 |
| Rate of aeration | 1 V.V.M. |
| Stirring | 400–600 rpm |

During the cultivation, the saccharide concentration in the culture modium was 0.001 to 0.080% (W/V) and the nitrogen concentration 0.09 to 0.15% (W/V). The protease potency of the culture liquor thus obtained was 550 P.U./ml.

EXAMPLE 4

A liquid medium (pH 7.0) containing 1.0% (W/V) of polypeptone, 0.5% (W/V) of soluble starch, 0.5% (W/V) of $KH_2PO_4$, 0.05%(W/V) of $MgSO_4$, 0.03%(W/V) of yeast extract, and 10% (W/V) of sodium chloride was sterilized at 120° C. for 10 minutes. Into a 3-liter jar fermenter, was charged 2 liters of the sterilized liquid medium. The liquid medium was then inoculated with a spore suspension (number of spores: $1.0 \times 10^6$/ml) of *Aspergillus sojae* ATCC 20823 (IAM 2703) collected from the malt extract medium of a slant culture. The inoculated medium was cultivated at 30° C. and an aeration rate of 1 V.V.M. with stirring at 500 rpm. The pH of the culture medium during cultivation was continually adjusted to about 7.0 with 5N $H_2SO_4$ and 5N NaOH.

When 48 hours had elapsed after the beginning of cultivation (that is, when proliferation of mold cells had been substantially terminated), 400 ml of the culture liquor was withdrawn from the outlet of the fermenter and the remaining culture liquor in the fermenter was quickly replenished with 400 ml of a protein-containing liquid medium of the following composition:

| | |
|---|---|
| Defatted soybean flour | 1.0% (W/V) |
| $KH_2PO$ 4 | 0.5 |
| Soluble starch | 0.5 |
| $MgSO_4$ | 0.05 |
| Yeast extract | 0.03 |
| Sodium chloride | 10 |
| Sterilization at 120° C. for 10 minutes. | |

The cultivation was continued under the following conditions, while repeating the above procedure every 12 hours:

| | |
|---|---|
| Temperature | 30° C. |
| pH of the culture medium | 7.0 |
| Rate of aeration | 1 V.V.M. |
| Stirring | 400–600 rpm |

The culture liquor on and after the third day of cultivation showed a saccharide concentration of 0.001 to 0.100% (W/V) and a nitrogen concentration of 0.08 to 0.15% (W/V). The thus intermittently obtained proteasecontaining culture liquors showed protease potencies as shown in Table 5.

TABLE 5

| Number of days | 1 | 2 | 3 | 4 | 5 | 6 |
|---|---|---|---|---|---|---|
| Potency (P.U./ml) of protease in culture liquor | 20 | 50 | 270 | 300 | 480 | 490 |

EXAMPLE 5

A liquid medium (1.5 liters) of the following composition was charged into a 2.5-liter mini jar fermenter and inoculated with *Aspergillus sojae* ATCC 20823 (IAM 2703) at a concentration of $10^6$ spores/ml.

| | % (W/V) |
|---|---|
| Soluble starch | 5.6 |
| Polypeptone | 0.5 |
| $MgSO_4.7H_2O$ | 0.2 |
| $K_2HPO_4$ | 0.38 |
| $KH_2PO_4$ | 0.12 |
| NaCl | 10.0 |

Cultivation was carried out under the following conditions:

| | |
|---|---|
| Temperature | 30° C. |
| pH of culture medium adjusted to 6.5–7.5 | |
| Dissolved oxygen (DO) adjusted to 3 mg/liter or above. | |

pH of culture medium adjusted to 6.5–7.5 Dissolved oxygen (DO) adjusted to 3 mg/liter or above.

After 2 or 3 days, when the proliferation of mold cells had substantially ceased, a liquid medium containing 5.6% (W/V) of soluble starch and 1.2% (W/V) of soybean flour was continuously added to the culture liquor at a dilution ratio of 0.015 to 0.020 and an equal amount of culture liquor was withdrawn.

The progress of cultivation was as shown in FIG. 1. As is seen from FIG. 1, during 15 days of continuous cultivation, the mold cell concentration was maintained at 8 to 14 g/liter. The protease activity was steadily in the range of from 400 to 500 PU/ml. During the period of continuous cultivation, the nitrogen concentration was in the range of from 0.025 to 0.03% (W/V).

What is claimed is:

1. In a process for producing protease by cultivating a protease-producing mold belonging to the genus Aspergillus in a liquid culture medium, wherein the improvement comprises continuously adding, in response to a measurement of total extracellular nitrogen, a liquid medium containing a protein material to the liquid culture medium after substantial termination of proliferation of the mold cells, in a manner which maintains the nitrogen concentration in the extracellular liquid culture medium at 0.05% (W/V) or below.

2. In a process for producing protease by cultivating a protease-producing mold belonging to the genus Aspergillus in a liquid culture medium, wherein the improvement comprises continuously adding, in response to a measurement of total extracellular nitrogen and saccharides, a liquid medium containing a protein material to the liquid culture medium after substantial termination of proliferation of the mold cells, in a manner which maintains the nitrogen concentration at 0.06–0.30% (w/v) and the saccharide concentration at 0.10% (W/V) or below in the extracellular liquid culture medium.

3. A process according to claim 1 wherein the protease-producing mold is *Aspergillus sojae* ATCC 20823 (IAM 2703), *Aspergillus sojae* IAM 2631, *Aspergillus oryzae* ATCC 20822 (IAM 2609), *Aspergillus oryzae* IFO 4176, or *Aspergillus tamarii* IAM 2156.

4. A process according to claim 2 wherein the protease-producing mold is *Aspergillus sojae* ATCC 20823 (IAM 2703), *Aspergillus sojae* IAM 2631, *Aspergillus oryzae* ATCC 20822 (IAM 2609), *Aspergillus oryzae* IFO 4176, or *Aspergillus tamarii* IAM 2156.

5. A process according to claim 2 wherein the saccharide concentration is maintained at 0.001–0.10% (W/V).

* * * * *